(12) United States Patent
Pedersen (10) Patent No.: US 10,733,267 B2
(45) Date of Patent: Aug. 4, 2020

(54) SURGICAL DATA CONTROL SYSTEM (71) Applicant: John Pedersen, Wadsworth, OH (US)

(72) Inventor: John Pedersen, Wadsworth, OH (US)

(73) Assignee: SURGICAL BLACK BOX LLC, Jackson, WY (US)

( * ) Notice: Subject to any disclaimer, the term of this patent is extended or adjusted under 35 U.S.C. 154(b) by 839 days.

(21) Appl. No.: 15/056,750

(22) Filed: Feb. 29, 2016

(65) Prior Publication Data

US 2016/0253472 A1    Sep. 1, 2016

Related U.S. Application Data

(60) Provisional application No. 62/126,059, filed on Feb. 27, 2015.

(51) Int. Cl.
*G06F 19/00* (2018.01)
*A61M 16/01* (2006.01)
(Continued)

(52) U.S. Cl.
CPC ........ *G06F 19/3418* (2013.01); *A61B 5/0002* (2013.01); *A61B 5/0013* (2013.01); *A61B 5/0022* (2013.01); *A61B 5/0084* (2013.01); *A61B 5/0205* (2013.01); *A61B 5/065* (2013.01); *A61B 5/1101* (2013.01); *A61B 5/4821* (2013.01); *A61B 5/6852* (2013.01); *A61B 5/6885* (2013.01); *A61B 90/361* (2016.02); *A61B 90/90* (2016.02); *A61M 16/01* (2013.01); *G06F 16/2455* (2019.01);

*G16H 15/00* (2018.01); *A61B 5/1172* (2013.01); *A61B 34/30* (2016.02); *A61B 2034/2059* (2016.02);
(Continued)

(58) Field of Classification Search
CPC . A61B 90/361; A61B 34/30; A61B 17/32002; A61B 2017/00415; A61N 1/3787; A61N 5/1001; A61N 5/1067; A61N 5/1075
See application file for complete search history.

(56) References Cited

U.S. PATENT DOCUMENTS

7,873,400 B2  1/2011  Moctezuma De La Barrera et al.
7,913,891 B2  3/2011  Doll et al.
(Continued)

*Primary Examiner* — Maroun P Kanaan
(74) *Attorney, Agent, or Firm* — Tarolli, Sundheim, Covell & Tummino LLP (57) ABSTRACT

One example a surgical data control system. A wireless data receiver receives surgical device data that is wirelessly transmitted from surgical instruments, medicine administering equipment, and energy delivery equipment during a surgical procedure. The surgical device data is stored in a memory system along with surgeon data, patient data, and environment data associated with the surgical environment in which the surgical procedure is performed. A report generator generates an aggregated surgical data set characterizing a relationship between the surgical device data, the surgeon data, the patient data, and the environment data. The report generator thus generates a surgical dashboard report comprising the aggregated surgical data set in a predetermined data format. The surgical data control system can transmit the surgical dashboard report to at least one remote device via a network upon conclusion of the surgical procedure.

19 Claims, 5 Drawing Sheets

(51) Int. Cl.
*G06F 17/30* (2006.01)
*A61B 5/00* (2006.01)
*G06F 16/2455* (2019.01)
*G16H 15/00* (2018.01)
*A61B 5/06* (2006.01)
*A61B 90/00* (2016.01)
*A61B 5/11* (2006.01)
*A61B 5/0205* (2006.01)
*A61B 90/90* (2016.01)
*A61B 34/20* (2016.01)
*A61B 5/1172* (2016.01)
*A61B 34/30* (2016.01)

(52) U.S. Cl.
CPC ..... *A61B 2090/064* (2016.02); *A61B 2505/05* (2013.01); *A61M 2205/3561* (2013.01); *A61M 2205/3592* (2013.01); *A61M 2205/50* (2013.01); *A61M 2205/702* (2013.01)

(56) References Cited

U.S. PATENT DOCUMENTS

| | | |
|---|---|---|
| 7,934,648 B2 | 5/2011 | Charles et al. |
| 8,087,584 B2 | 1/2012 | Grimard |
| 8,558,880 B2 | 10/2013 | Nambakam et al. |
| 8,628,518 B2 | 1/2014 | Blumenkranz et al. |
| 2002/0165541 A1 | 11/2002 | Whitman |
| 2006/0085222 A1 | 4/2006 | Huang et al. |
| 2006/0119481 A1 | 6/2006 | Tethrake et al. |
| 2007/0027459 A1 | 2/2007 | Horvath et al. |
| 2009/0076349 A1 | 3/2009 | Libbus et al. |
| 2010/0076455 A1 | 3/2010 | Birkenbach et al. |
| 2010/0249540 A1 | 9/2010 | Lisogurski |
| 2010/0262139 A1 | 10/2010 | Beller et al. |
| 2011/0125138 A1 | 5/2011 | Malinouskas et al. |
| 2011/0157480 A1 | 6/2011 | Curl |
| 2012/0209257 A1* | 8/2012 | van der Weide .. A61B 18/1815 606/23 |
| 2012/0232540 A1 | 9/2012 | Baur et al. |
| 2012/0265196 A1 | 10/2012 | Turner et al. |
| 2013/0238330 A1* | 9/2013 | Casella dos Santos ..... G10L 15/183 704/235 |
| 2013/0253480 A1 | 9/2013 | Kimball et al. |
| 2014/0081659 A1* | 3/2014 | Nawana ................ G16H 50/20 705/3 |
| 2014/0257047 A1 | 9/2014 | Sillay et al. |
| 2014/0320272 A1 | 10/2014 | Druzinic-Fiebach |
| 2014/0353188 A1* | 12/2014 | Reschke ................ A61B 50/30 206/363 |
| 2014/0378961 A1 | 12/2014 | Fischer et al. |

\* cited by examiner

SURGICAL DATA CONTROL SYSTEM

RELATED APPLICATIONS

This application claims priority from U.S. Provisional Patent Application Ser. No. 62/126,059, filed 27 Feb. 2015, which is incorporated herein in its entirety.

TECHNICAL FIELD

The present disclosure relates generally to surgical procedures, and specifically to a surgical data control system.

BACKGROUND

The healthcare industry is becoming increasingly more competitive, and has been the subject of increases in a wide variety of innovations. In particular, in a surgical environment, it is highly necessary to manage a large number of different factors that provide both life-sustaining capabilities for a patient, particularly when induced to an unconscious state, while still performing complex and precise surgical procedures. In the United States alone, over one hundred million surgeries are performed each year. In a large number of those surgeries (e.g., approximately 6%), complications resulting from the surgery can occur. Complications resulting from surgery can cause great difficulties for patients, such as loss of quality of life or even life itself. Such complications can also result in large financial expense, such as based on legal costs incurred by healthcare providers, and in turn, increased healthcare costs. As a result, avoiding complications that result from surgery is of great concern to healthcare providers.

SUMMARY

One example includes a surgical data control system. The system includes a wireless data receiver configured to receive surgical device data. The surgical device data includes surgical instrument data transmitted from a plurality of surgical instruments. The surgical instrument data from each of the plurality of surgical instruments characterizes at least one metric associated with performance and function of a respective one of the plurality of surgical instruments during a surgical procedure on a patient. The surgical device data also includes medicine administration data transmitted from medicine administering equipment. The medicine administration data characterizes at least one of dosage and time of medicine administered to the patient via the medicine administering equipment during the surgical procedure. The surgical device data further includes energy data transmitted from at least one energy providing device. The energy data characterizes operation of the at least one energy providing device during the surgical procedure. The system also includes a memory system configured to store the surgical device data, surgeon data associated with at least one surgeon performing the surgical procedure, patient data associated with the patient, and environment data associated with the surgical environment in which the surgical procedure is performed. The system further includes a report generator configured to generate an aggregated surgical data set characterizing a relationship between the surgical device data, the surgeon data, the patient data, and the environment data. The report generator is also configured to generate a surgical dashboard report comprising the aggregated surgical data set in a predetermined data format. The surgical data control system can be configured to transmit the surgical dashboard report to at least one remote device via a network upon conclusion of the surgical procedure.

Another example includes a surgical system comprising a plurality of surgical instruments. Each of the plurality of surgical instruments includes a surgical instrument data controller. The surgical instrument controller includes a registration component configured to register a given surgeon or staff to the respective one of the plurality of surgical instruments during use of the respective one of the plurality of surgical instruments by the given surgeon in a surgical procedure. The surgical instrument controller also includes a data collection sensor configured to measure surgical instrument data comprising at least one of pressure, tension, and torque associated with use of the respective one of the plurality of surgical instruments by the given surgeon during the surgical procedure. The surgical instrument controller also includes a real-time clock configured to provide time-stamp data associated with at least one of the registration of the given surgeon to the respective one of the plurality of surgical instruments and the surgical instrument data associated with the respective one of the plurality of surgical instruments. The surgical instrument controller further includes a transceiver configured to transmit the surgical instrument data associated with the respective one of the plurality of surgical instruments to a surgical data control system, the surgical data control system being configured to store the surgical instrument data for reporting and feedback associated with the surgical procedure.

Another example includes a method for providing feedback for a surgical procedure performed by at least one surgeon. The method includes wirelessly receiving surgical instrument data that is transmitted from a plurality of surgical instruments. The surgical instrument data from each of the plurality of surgical instruments can characterize at least one of pressure, tension, and torque associated with use of the respective one of the plurality of surgical instruments by a given surgeon of the at least one surgeon during the surgical procedure. The method also includes storing the surgical instrument data, surgeon data associated with at least one surgeon performing the surgical procedure, patient data associated with the patient, and environment data associated with the surgical environment in which the surgical procedure is performed in a memory system. The method also includes graphically providing real-time surgical feedback to the at least one surgeon during the surgical procedure based on the surgical instrument data associated with each of the plurality of surgical instruments. The method also includes providing an indicator alarm to the at least one surgeon during the surgical procedure in response to the surgical instrument data having a respective value outside of an acceptable threshold range. The method also includes generating an aggregated surgical data set characterizing a relationship between the surgical instrument data, the surgeon data, the patient data, and the environment data. The method further includes generating a surgical dashboard report comprising the aggregated surgical data set in a predetermined data format, and transmitting the surgical dashboard report to at least one remote device via a network upon conclusion of the surgical procedure.

DETAILED DESCRIPTION

The present disclosure relates generally to surgical procedures, and specifically to a surgical data control system. The surgical data control system can be implemented in a variety of surgical environments, including inpatient surgery, outpatient surgery, laparoscopic surgery, open surgeries, or any other of a variety of medical procedures. The surgical data control system can include a data receiver that is configured to wirelessly receive surgical device data that is transmitted from a variety of surgical devices that are implemented in the surgical procedure on a patient. The surgical device data can include surgical instrument data that is associated with at least one metric associated with function and performance of the respective surgical instrument, such as at least one of torque, tension, and pressure. The surgical instruments can be any of a variety of standard surgical instruments, and can be adapted to receive a surgical instrument data controller that can, among other functions, collect the at least one metric and wirelessly transmit the at least one metric to the surgical data control system. The surgical device data can also include medicine administration data associated with medicine that is administered to the patient, and energy data associated with energy providing devices (e.g., cautery devices).

The surgical data control system also includes a memory system configured to store the surgical device data, as well as surgeon data associated with one or more surgeons that are performing the surgical procedure, patient data (e.g., metrics and medical history associated with the patient), and environment data associated with the environment of the surgical procedure (e.g., the operating room, such as including temperature, lighting, and humidity). As an example, the data stored in the memory system, such as the surgical device data, can be monitored in real-time by the surgical data control system. For example, the surgical data control system can provide the surgical device data in a graphical feedback manner in real-time to the surgeon(s). Therefore, a graphical feedback system can provide an alarm in response to a respective one of the parameters associated with the surgical device data having a value that is outside of a predetermined threshold range of values.

The surgical data control system further includes a report generator that is configured to aggregate the data stored in the memory system to provide a relationship between the surgical device data, the surgeon data, the patient data, and the environment data, such as to provide usage, timing, and association between the surgeon(s) and the surgical devices. The report generator can thus generate a surgical dashboard report from the aggregated data set that includes the relationship between the surgical device data, the surgeon data, the patient data, and the environment data, such as to provide usage, timing, and association between the surgeon(s) and the surgical devices. As an example, the surgical dashboard report can be converted to a predetermined data format (e.g., portable document format (PDF)) and can be wirelessly transmitted to one or more devices via a network, such as to the healthcare facility, insurance company facility, and/or to computer devices associated with the patient or other authorized people.

Figure 1:
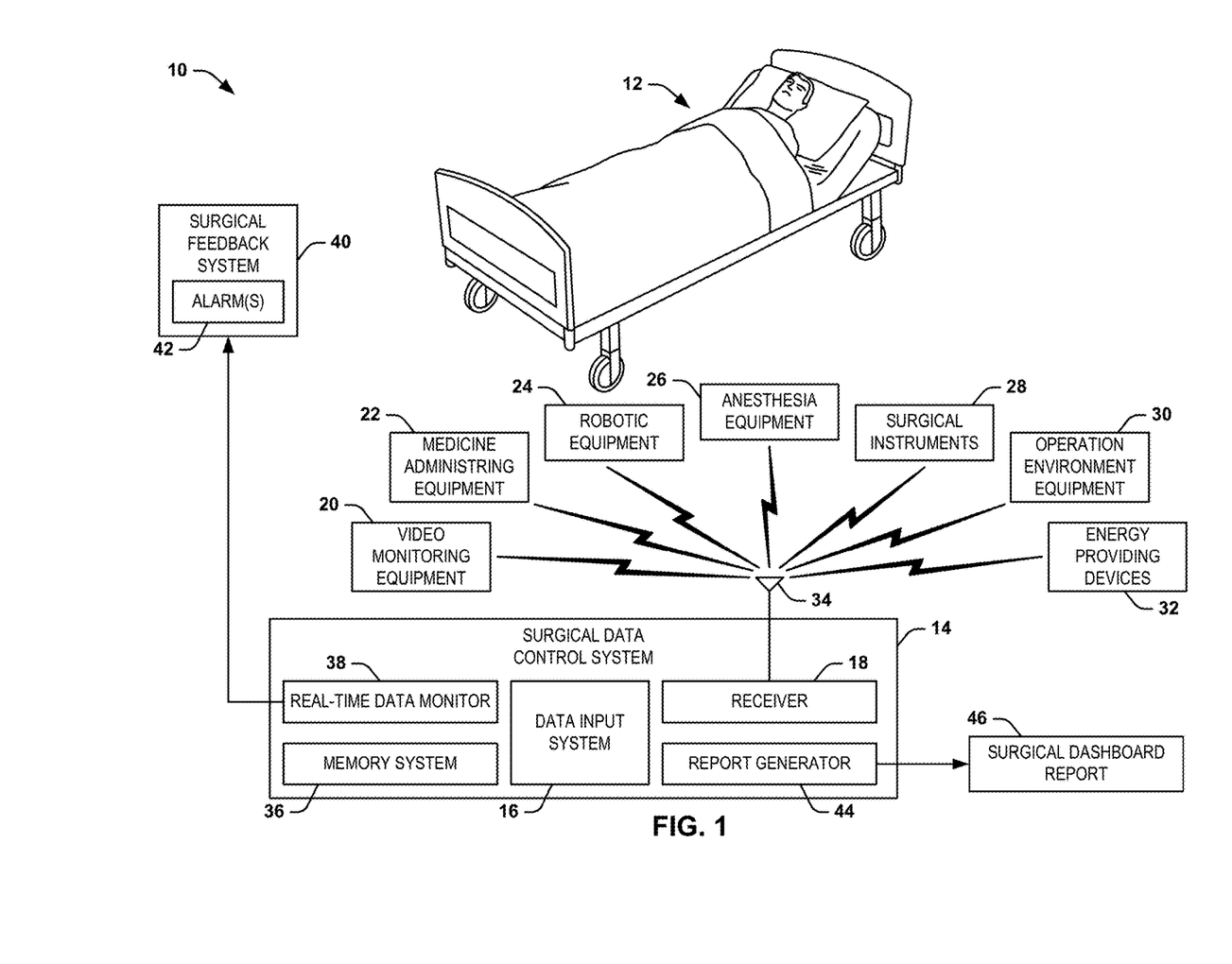
FIG. 1 illustrates an example of a surgical system.

FIG. 1 illustrates an example of a surgical system 10. The surgical system 10 demonstrates a patient 12 undergoing a surgical procedure that is performed by one or more surgeons, such as in an operating room of a healthcare facility. As an example, the surgical procedure can be any of a variety of surgical or medical procedures, such as an inpatient surgery, an outpatient surgery, a laparoscopic surgery, open surgeries, or any other of a variety of medical procedures.

In the example of FIG. 1, the surgical system 10 demonstrates a surgical data control system 14. As an example, the surgical data control system 14 can be configured as or as part of a central computer system that is located in the operating room or is accessible from the operating room, such as via a network (e.g., a local area network (LAN)). The surgical data control system 14 includes a data input system 16 that can be arranged as any of a variety of input devices to receive surgeon data and patient data. The surgeon data can include data regarding one or more surgeons that are performing the surgical procedure, such as identification data, experience, contact information, or any other information associated with the surgeon(s). The patient data can include a variety of information about the patient 12, such as biographical data (e.g., metrics that include age, height, weight, mass-body index (BMI), insurance information, family contacts, etc.), medical history data (e.g., prior procedures, past and current medication, family history, etc.), and/or known allergies. The data input system 16 can also include data associated with surgical staff (e.g., nurses, assistants, operating room maintenance, etc.). For example, the surgeon(s) and/or staff can enter the respective surgeon data, patient data, and/or staff data into the data input system 16 through a keyboard, voice recognition interface, or a variety of other input means.

The surgical data control system 14 also includes a receiver 18. The receiver 18 can be configured as a wireless receiver (e.g., operating on Bluetooth, Wi-Fi, or any of a variety of other wireless protocols) that is configured to receive surgical device data from a variety of surgical devices, instruments, and components that are utilized during the surgical procedure. In the example of FIG. 1, the surgical system 10 demonstrates video monitoring equipment 20, medicine administering equipment 22, robotic equipment 24, anesthesia equipment 26, surgical instruments 28, operation environment equipment 30, and energy providing devices 32 that are all in wireless communicative contact with the receiver 18 via an antenna 34. While the surgical system 10 in the example of FIG. 1 demonstrates all of these components as part of the surgical procedure, it is to be understood that the surgical procedure is not limited to including all of the surgical components demonstrated in the surgical system 10. Additionally, one or more components that are implemented in the surgical procedure can be included as part of more than one of the separate surgical components demonstrated in the surgical system 10. Furthermore, the surgical components demonstrated in the surgical system 10 are not all limited to providing data via a wireless connection, but could instead provide data via a wired connection to the surgical data control system 14, or can be provided as static values to the surgical data control system 14 (e.g., via the data input system 16). Therefore, the surgical system 10 demonstrates the video monitoring equipment 20, the medicine administering equipment 22, the robotic equipment 24, the anesthesia equipment 26, the surgical instruments 28, the operation environment equipment 30, and the energy providing devices 32 by example only.

The video monitoring equipment 20 can be configured as one or more recording devices that can monitor the surgical procedure in real-time. As an example, the video monitoring equipment 20 can be configured as one or more video cameras that can record a real-time video feed of at least a portion of the surgical procedure, such as from different angle perspectives. As another example, the video monitoring equipment 20 can include cameras that are attached to the distal end of one or more probes (e.g., catheters or scopes) to capture a video feed of internal portions of the anatomy of the patient 12. As another example, the video monitoring equipment 20 can include cameras that are configured to capture static, still photographs of the surgical procedure, such as to capture closer details of the surgical procedure than can be permitted by certain video recording devices. As yet another example, the video monitoring equipment 20 can also include audio, such as a real-time audio recording of the surgical procedure, dictated notes provided by the surgeon(s) or the staff, or of the patient 12 (e.g., vocal feedback of the patient 12, patient vitals (e.g., heartbeat or respiration), etc.). Thus, the video monitoring equipment 20 can collectively and continuously transmit audio/video data wirelessly to the surgical data control system 14 during the surgical procedure.

The medicine administering equipment 22 can be configured to administer medication to the patient 12. For example, the medicine administering equipment 22 can include intravenous (IV) medication administering equipment that can be configured to track a volume of liquid that is administered to the patient 12. As another example, the medicine administering equipment 22 can include gas medication or oxygen-providing equipment that can be configured to track a volume of gas or oxygen that is administered to the patient 12. The medicine administering equipment 22 can thus be configured to track an amount of medication that is administered to the patient 12 during the surgical procedure, and can wirelessly transmit the amount and type of medication as medicine administration data to the surgical data control system 14 in real-time during the surgical procedure.

The robotic equipment 24 can correspond to one or more electro-mechanical devices or components that are configured to assist the surgeon(s) during the surgical procedure. As an example, the robotic equipment 24 can be configured to provide pressure or apply torque to hold open a wound or incision, to move large medical equipment throughout the surgical environment, to adjust positioning of the patient, or any of a variety of other functions that require mechanical motion or stability. The robotic equipment 24 can thus be configured to wirelessly transmit robot input data to the surgical data control system 14, such as including pressure, torque, position, maintenance scheduling, or any other data that is pertinent to the operation of the robotic equipment 24 during the surgical procedure in real-time, or that is pertinent to the maintenance of the robotic equipment 24.

The anesthesia equipment 26 can be configured to administer anesthetic to the patient 12 to numb at least a portion of the anatomy of the patient 12 or to induce a sleeping state of the patient 12. For example, the anesthesia equipment 26 can include IV medication administering equipment that can be configured to track a volume of anesthetic that is administered to the patient 12. Additionally, the anesthesia equipment 26 can be configured to monitor vital signs of the patient 12, such as heart rate, respiration, blood-pressure, or any of a variety of other vital information with respect to the patient. Therefore, the anesthesia equipment 26 can be configured to wirelessly transmit anesthesia data to the surgical data control system 14 during the surgical procedure in real-time.

The surgical instruments 28 can be configured as any of a variety of hand-held and other surgical instruments that are implemented or manipulated by the surgeon(s) or staff during the surgical procedure. Each of the surgical instruments 28 can be configured to measure surgical instrument data corresponding to at least one metric associated with performance and function of the respective surgical instrument. As an example, the surgical instrument data can include at least one of pressure, torque, or tension associated with the manipulation of the respective surgical instrument on the patient 12. As another example, one or more of the surgical instruments 28 can be configured to detect a tissue type (e.g., bone, muscle, skin, fat, etc.) of the patient 12 during use, such that the tissue type can correspond to the at least one metric. As yet another example, one or more of the surgical instruments 28 can be configured to detect position of the surgical instrument 28 in three-dimensional space or relative to a reference position, or can be configured to detect motion (e.g., hand tremors), such that the position or motion can correspond to the at least one metric.

Each of the surgical instruments 28, for example, can be adapted to include a surgical instrument data controller, as described in greater detail herein, that is configured to collect the respective surgical instrument data and to wirelessly transmit the surgical instrument data to the surgical data control system 14. As one example, the surgical instruments 28 can be manufactured or otherwise fabricated to include the surgical instrument data controller. As another example, the surgical instrument data controller can correspond to a separate component that includes sensing means for measuring the surgical instrument data and a transceiver for receiving data and for transmitting the surgical instrument data. As described in greater detail herein, the surgical instrument data can correlate use of the respective surgical instrument, as well as the at least one metric associated with the performance and function of the respective surgical instrument during the surgical procedure, with a specific time and identity of the surgeon or staff member that used the respective surgical instrument. Accordingly, each of the surgical instruments 28 can transmit the surgical instrument data to the surgical data control system 14 to provide a large amount and variety of data associated with the use of the surgical instruments 28 during the surgical procedure.

The operation environment equipment 30 can correspond to the equipment associated with maintaining or providing the surgical environment. As an example, the operation environment equipment 30 can provide an environment that is suitable and safe for the performance of the surgical procedure. As an example, the surgical environment can correspond to an operating room. Therefore, the operation environment equipment 30 can include lights, a thermostat, a humidifier, an air filter, fans, or any of a variety of other equipment. Thus, the operation environment equipment 30 can also include a variety of equipment that can measure the environment conditions of the operating room, such as an amount of illumination, temperature, humidity, air purity, or other environmental factors. The operation environment equipment 30 can thus be adapted to provide (e.g., wirelessly) the measured environment conditions to the surgical data control system 14 in real-time during the surgical procedure.

The energy providing devices 32 can correspond to devices that provide power to implement a function during the surgical procedure. For example, the energy providing devices 32 can correspond to cautery devices that are implemented to cauterize a wound after completion of an internal portion of the surgical procedure. As another example, the energy providing devices 32 can correspond to radiology equipment that provides imaging of the patient 12 during the surgical procedure. Therefore, the energy providing devices 32 can wirelessly transmit energy data associated with use of the energy providing devices 32 (e.g., power consumption, intensity, etc.) to the surgical data control system 14 in real-time during the surgical procedure.

The previous descriptions of the video monitoring equipment 20, the medicine administering equipment 22, the robotic equipment 24, the anesthesia equipment 26, the surgical instruments 28, the operation environment equipment 30, and the energy providing devices 32 are by example, and are not intended to be limited to the subclassifications described herein. As an example, some surgical devices can be suitably classified in more than one of the categories described previously regarding the video monitoring equipment 20, the medicine administering equipment 22, the robotic equipment 24, the anesthesia equipment 26, the surgical instruments 28, the operation environment equipment 30, and the energy providing devices 32. As another example, other surgical devices that have not been described in one of the categories can likewise be configured to transmit operational data to the surgical data control system 14. Therefore, the example of the surgical devices that can transmit, wirelessly or otherwise, is not intended to be limited to as described herein.

The surgical data control system 14 also includes a memory system 36 that is configured to store and maintain the surgical device data that is transmitted by the video monitoring equipment 20, the medicine administering equipment 22, the robotic equipment 24, the anesthesia equipment 26, the surgical instruments 28, the operation environment equipment 30, and the energy providing devices 32. The memory system 36 can also store the data that is input via the data input system 16, such as including the patient data, the surgeon data, and the staff data. The memory system 36 can be accessed by a real-time data monitor 38 to provide real-time monitoring of the data stored in the memory system 16 (e.g., the surgical device data), such as to provide surgical feedback.

In the example of FIG. 1, the surgical system 10 demonstrates a surgical feedback system 40. The surgical feedback system 40 can be configured, for example, as one or more video monitors to provide graphical feedback of the surgical procedure, such as based on the monitoring of the surgical device data via the real-time data monitor 38. As an example, the real-time data monitor 38 can transmit (e.g., wirelessly) the surgical device data to the surgical feedback system 40, such that the surgical feedback system 40 can display the surgical device data to the surgeon(s) and/or staff during the surgical procedure. As an example, the memory system 36 can be provided with a set of predetermined threshold data that defines a predetermined threshold range of operation of the surgical device data, such as associated with one or more of the video monitoring equipment 20, the medicine administering equipment 22, the robotic equipment 24, the anesthesia equipment 26, the surgical instruments 28, the operation environment equipment 30, and the energy providing devices 32. For example, the predetermined threshold data can be provided to the surgical data control system 14 via the data input system 16 or via a network prior to the beginning of the surgical procedure, or can be provided during the surgical procedure.

Therefore, the real-time data monitor 38 can be configured to continuously monitor the surgical device data relative to the predetermined threshold data in real-time during the surgical procedure. In response to one or more of the values of the surgical device data exceeding (above or below) the predetermined threshold range of operation, the real-time data monitor 38 can provide an indication to the surgical feedback system 40 of an aberration or breach in the value(s) of the surgical device data relative to the predetermined threshold data. In response, the surgical feedback system 40 can provide a graphical and/or audial indication to the surgeon(s) and/or the staff via one or more alarms 42 to provide notice of the aberration or breach in the value(s) of the surgical device data relative to the predetermined threshold data. Accordingly, the surgeon(s) and/or the staff can provide corrective measures in a rapid reactive manner based on the real-time monitoring of the surgical device data via the real-time data monitor 38 and the surgical feedback system 40.

In addition, the surgical data control system 14 includes a report generator 44. The report generator 44 is configured to access the data stored in the memory system 36, such as immediately upon conclusion of the surgical procedure to aggregate the set of data stored in the memory system 36. The aggregation of the set of data stored in the memory system 36 can provide a relationship between substantially all aspects of the surgical procedure, with respect to the patient data, the surgeon data, the staff data, and all of the surgical device data. For example, the aggregation performed by the report generator 44 can associate temporal data and unique identifiers associated with the video monitoring equipment 20, the medicine administering equipment 22, the robotic equipment 24, the anesthesia equipment 26, the surgical instruments 28, the operation environment equipment 30, and the energy providing devices 32 to the surgeon(s) and/or staff and to the patient to provide interrelationships therein.

Upon aggregating the data stored in the memory system 36, the report generator 44 can generate a surgical dashboard report 46 of the surgical procedure. The surgical dashboard report 46 can provide the aggregated data set in a single data source, such as a uniform resource locator (URL) or in a data file. As an example, the data file associated with the surgical dashboard report 46 can be generated in a predetermined data format, such as portable data format (PDF) that is widely accessible via substantially any computer system. For example, the PDF document corresponding to the surgical dashboard report 46 that is generated by the report generator 44 can include hyperlinks to provide access to additional information and/or video data (e.g., the video stream(s) provided via the video monitoring equipment 20) of one or more aspects of the surgical procedure.

Thus, the surgical data control system 14 can be configured to transmit (e.g., via a network) the surgical dashboard report 46 to one or more devices to facilitate viewing by interested parties. For example, the surgical data control system 14 can transmit the surgical dashboard report 46 to one or more enterprise servers associated with the healthcare facility, to one or more enterprise servers associated with an insurance company associated with the patient 12, and/or to one or more computer devices (e.g., personal computer, laptop computer, tablet computer, smart-phone, etc.) to the patient 12 and/or to one or more patient-authorized other people (e.g., via email or as downloadable via a network location). Accordingly, the surgical dashboard report 46 that provides a complete report of the relationship between substantially all aspects of the surgical procedure, with respect to the patient data, the surgeon data, the staff data, and all of the surgical device data, can be generated and transmitted to all necessary parties substantially immediately (e.g., within one or a few seconds) after conclusion of the surgical procedure.

As an example, the surgical dashboard report 46 can provide a comprehensive description of the surgical procedure to the patient and to the family of the patient to provide a greater understanding of the aspects of the surgical procedure. As another example, the surgical dashboard report 46 can be utilized by administration of the healthcare facility to provide accountability of all aspects of the surgical procedure with respect to the surgeon(s) and/or the staff. As another example, surgical dashboard report 46 can be implemented by insurance companies to make decisions as to billing practices and/or coverage with respect to the patient 12 and/or future patients. As yet another example, the surgical dashboard report 46 can be utilized by the healthcare facility for research and/or as a teaching tool for surgeons and/or staff, or to optimize performance of future surgical procedures. Accordingly, the surgical system 10 and the surgical dashboard report 46 can provide a number of important purposes for providing healthcare and substantially minimizing complications that may arise from performing a given surgical procedure.

Figure 2:
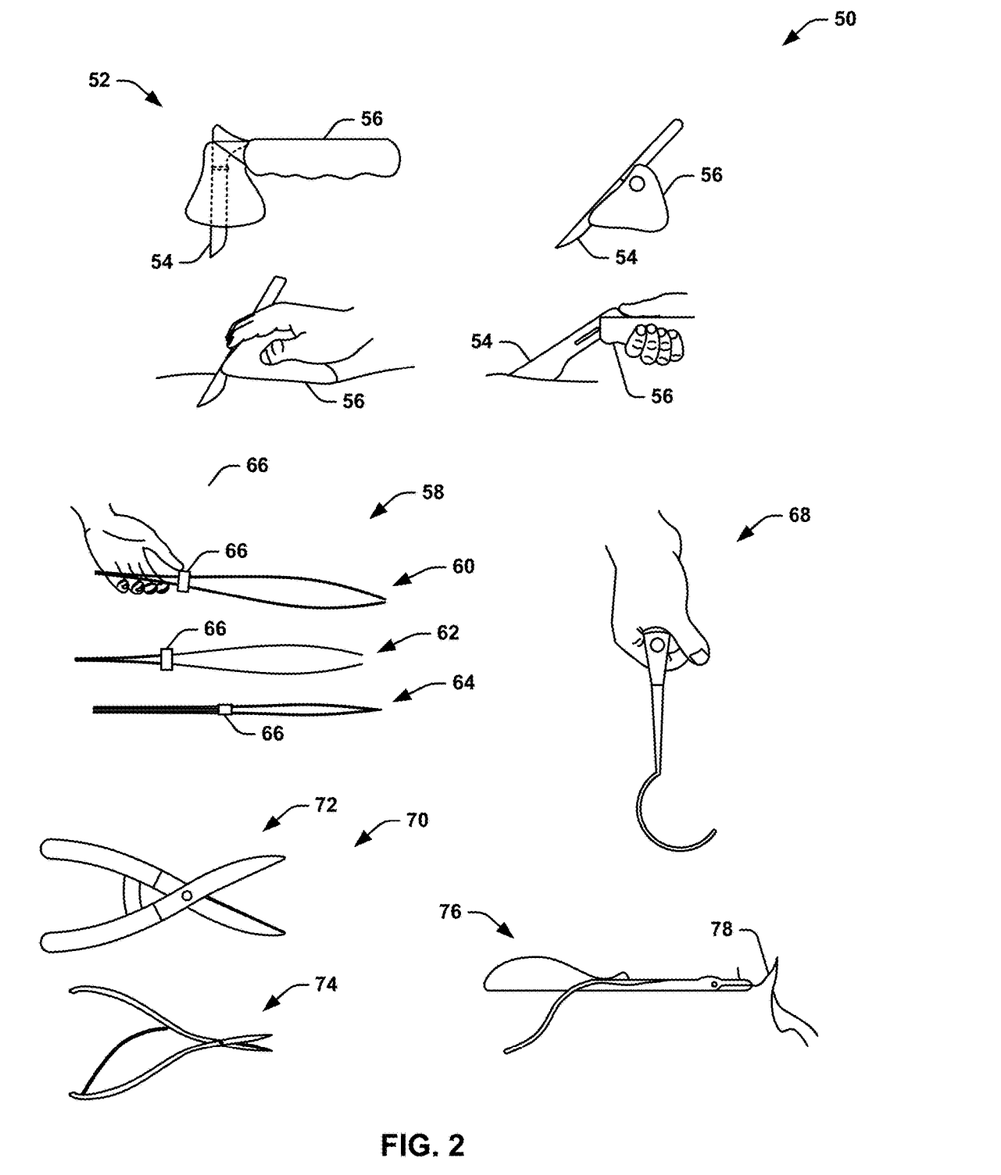
FIG. 2 illustrates an example diagram of surgical instruments.

As described previously, the surgical instruments 28 can be configured as any of a variety of hand-held and other surgical instruments that are implemented or manipulated by the surgeon(s) or staff during the surgical procedure. FIG. 2 illustrates an example diagram 50 of surgical instruments. The surgical instruments depicted in the diagram 50 are demonstrated by example, such that the diagram 50 is not intended to be an exhaustive collection of surgical instruments.

The diagram 50 includes a set of scalpel devices 52 that are demonstrated in the example of FIG. 2 as a set of scalpels 54 and scalpel holders 56 configured to hold the respective scalpels 54 in place to facilitate use of the scalpels 54 via the scalpel holders 56. As an example, each of the scalpel holders 56 can be adapted to include a surgical instrument data controller. As an example, the scalpel holders 56 can be fabricated to include a surgical instrument data controller integral with the design. As another example, the scalpel holders 56 or the scalpels 54 themselves can be configured to attach to a surgical instrument data controller that is arranged as a separate unit, such as having been designed and dimensioned to attach to the respective one of the scalpel 54 or scalpel holder 56. Therefore, the scalpels 54 and/or the scalpel holders 56 can measure at least one metric (e.g., torque, pressure, and/or tension) associated with use of the scalpel 54. The scalpels 54 and scalpel holders 56 are demonstrated merely by example, such that other designs of scalpels 54 and scalpel holders 56 can be implemented in the surgical system 10, as described herein.

The diagram 50 also includes a set of clamps 58 that can be implemented for a variety of surgical reasons. The clamps 58 are demonstrated as hand-held at 60, in an open state at 62, and in a closed state at 64. As an example, the clamps 58 can be switched between the open state 62 and the closed state 64 based on a sliding element 66 that can provide a closing force on the clamps 58. As an example, the clamps 58 can be fabricated to include a surgical instrument data controller integral with the design (e.g., associated with the sliding element 66), or can be configured to attach to a surgical instrument data controller that is arranged as a separate unit, such as having been designed and dimensioned to attach to the respective clamps 58. Therefore, the clamps 58 can measure at least one metric (e.g., torque, pressure, and/or tension) associated with use of the clamps 58. The clamps 58 are demonstrated merely by example, such that other designs of clamps 58 can be implemented in the surgical system 10, as described herein.

The diagram 50 also includes a retractor 68, demonstrated as hand-held, that can be implemented for a variety of surgical reasons. As an example, the retractor 68 can be fabricated to include a surgical instrument data controller integral with the design, or can be configured to attach to a surgical instrument data controller that is arranged as a separate unit, such as having been designed and dimensioned to attach to the respective retractor 68. Therefore, the retractor 68 can measure at least one metric (e.g., torque, pressure, and/or tension) associated with use of the retractor 68. The retractor 68 is demonstrated merely by example, such that other designs of retractors 68 can be implemented in the surgical system 10, as described herein.

The diagram 50 also includes a set of scissors 70 that can be implemented for a variety of surgical reasons. The scissors 70 are demonstrated as including a first type with a spring-chamber at 72, and a second type with a spring-steel element at 74. As an example, the scissors 70. As an example, the scissors 70 can be fabricated to include a surgical instrument data controller integral with the design (e.g., associated with the respective spring types), or can be configured to attach to a surgical instrument data controller that is arranged as a separate unit, such as having been designed and dimensioned to attach to the respective scissors 70. Therefore, the scissors 70 can measure at least one metric (e.g., torque, pressure, and/or tension) associated with use of the scissors 70. The scissors 70 are demonstrated merely by example, such that other designs of scissors 70 can be implemented in the surgical system 10, as described herein.

The diagram 50 also includes a needle-holder 76, demonstrated as holding a curved needle 78, that can be implemented for a stitching wounds or incisions. As an example, the needle-holder 76 can be fabricated to include a surgical instrument data controller integral with the design, or can be configured to attach to a surgical instrument data controller that is arranged as a separate unit, such as having been designed and dimensioned to attach to the respective needle-holder 76. Therefore, the needle-holder 76 can measure at least one metric (e.g., torque, pressure, and/or tension) associated with use of the needle-holder 76. The needle-holder 76 is demonstrated merely by example, such that other designs of needle-holder 76 can be implemented in the surgical system 10, as described herein.

Figure 3:
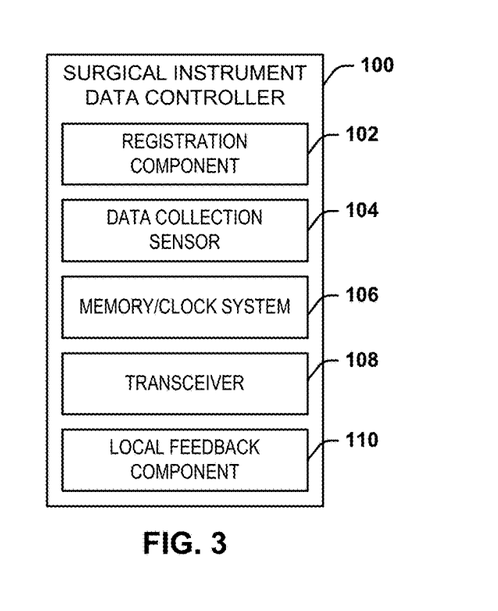
FIG. 3 illustrates an example of a surgical instrument data controller.

FIG. 3 illustrates an example of a surgical instrument data controller 100. The surgical instrument data controller 100 can correspond to a surgical instrument data controller that can be manufactured integrally with respect to any of the surgical instruments 28 (e.g., any of the surgical instruments in the diagram 50 of the example of FIG. 2). Therefore, reference is to be made to the example of FIGS. 1 and 2 in the following description of the example of FIG. 3. While the discussion herein describes use of the surgical instrument data controller 100 with respect to the surgical instruments 28, it is to be understood that the surgical instrument data controller 100 can likewise be adapted for any of the other surgical devices described in the example of FIG. 1.

The surgical instrument data controller 100 includes a registration component 102 configured to register a surgeon or staff member to use of the surgical instrument 28 during the surgical procedure. As an example, the registration component 102 can include a sensor with which the surgeon or staff can interact to provide an indication that the surgical instrument 28 is currently in use by the respective surgeon or staff. For example, the registration component 102 can include a radio-frequency identification (RFID) tag or sensor with which the surgeon or staff can interact with a corresponding RFID sensor or tag, respectively. As another example, the registration component 102 can include a finger/thumb print sensor configured to allow the surgeon or staff to provide a unique indication of user to the surgical instrument data controller 100. Thus, in response to the registration of the surgeon or staff via the registration component 102, the surgical instrument data controller 100 can identify the current user of the surgical instrument 28.

The surgical instrument data controller 100 also includes a data collection sensor 104. The data collection sensor 104 is configured to measure surgical instrument data corresponding to the at least one metric associated with performance and function of the respective surgical instrument 28. As an example, the surgical instrument data can include at least one of pressure, torque, or tension associated with the manipulation of the respective surgical instrument on the patient 12. As another example, one or more of the surgical instruments 28 can be configured to detect a tissue type (e.g., bone, muscle, skin, fat, etc.) of the patient 12 during use, such that the tissue type can correspond to the at least one metric. As yet another example, one or more of the surgical instruments 28 can be configured to detect position of the surgical instrument 28 in three-dimensional space or relative to a reference position, or can be configured to detect motion (e.g., hand tremors), such that the position or motion can correspond to the at least one metric. The collection of the surgical instrument data can be continuous in real-time, such as in response to registration of a given one of the surgeon or staff.

The surgical instrument data controller 100 also includes a memory/clock system 106. The memory/clock system 106 can be configured to operate in conjunction with the registration component 102 and the data collection sensor 104 to provide time-stamp information associated with registration of the surgical instrument 28 via the registration component 102 and/or time-stamp information associated with the collection of the surgical instrument data via the data collection sensor 104. The registration of the surgical instrument 28 and the collected surgical instrument data can be stored in the memory/clock system 106, such as for feedback purposes and for transmission, as described in greater detail herein.

The surgical instrument data controller 100 also includes a transceiver 108. The transceiver 108 is configured to access the memory/clock system 106 to wirelessly transmit the surgical instrument data to the surgical data control system 14, with the surgical instrument data also including the registration data associated with the registration of the surgical instrument 28. As an example, the transceiver 108 can be configured to transmit the surgical instrument data substantially continuously in real-time, or can transmit the surgical instrument data at conclusion of registration/use of the surgical instrument 28 and/or at conclusion of the surgical procedure.

In addition, the transceiver 108 can be configured to receive data. As an example, the transceiver 108 can be configured to transmit the surgical instrument data to a transceiver 108 associated with a separate surgical instrument data controller 100 corresponding to a respective separate surgical instrument 28. For example, the transceiver 108 can provide a shorter-range transmission of the surgical instrument data, and thus with less power to conserve power (e.g., less battery power), by transmitting the surgical instrument data to transceivers 108 in separate surgical instrument data controllers of separate surgical instruments 28 in a sequential chain before the surgical instrument data is received by the receiver 18 of the surgical data control system 14. In addition or in alternative, the surgical instrument data can be transmitted to transceivers 108 in separate surgical instrument data controllers of separate surgical instruments 28 to provide redundancy in collection of the surgical instrument data, such that the surgical instrument data of other surgical instruments 28 can be stored in the memory/clock system 106 of the surgical instrument data controller 100. Therefore, the surgical instrument data can be propagated throughout the surgical instrument data controllers 100 of a plurality of surgical instruments 28.

Furthermore, the surgical instrument data controller 100 includes a local feedback component 110. As an example, the local feedback component 110 can correspond to an indicator (e.g., a buzzer, a light (e.g., LED), a haptic feedback system, etc.) to provide an indication to the surgeon or staff that is using the surgical instrument 28. As an example, the transceiver 108 can receive predetermined threshold data associated with a predetermined range of acceptable operation of the surgical instrument 28, as associated with the surgical instrument data that is collected via the data collection sensor 104. The predetermined threshold data can thus be saved in the memory/clock system 106. Therefore, in response to one or more of the values of the surgical instrument data exceeding (above or below) the predetermined threshold range of operation, the local feedback component 110 (e.g., based on a microcontroller or processing component) can provide a local or global indication to the surgeon or staff of an aberration or breach in the value(s) of the surgical instrument data relative to the predetermined threshold data. Additionally, the indication of the aberration or breach in the value(s) of the surgical instrument data relative to the predetermined threshold data can likewise be saved in the memory/clock system 106 and/or transmitted to the surgical data control system 14 via the transceiver.

The surgical instrument data controller 100 is demonstrated in the example of FIG. 3 by example. Therefore, the surgical instrument data controller 100 is not intended to be limited to the example of FIG. 3. For example, the surgical instrument data controller 100 can include additional functionality and/or capability associated with monitoring or use in the surgical procedure, such as can be stored in the memory/clock system 106 and/or transmitted as the surgical instrument data via the transceiver 108. As another example, the surgical instrument data controller 100 is not limited to including all of the elements of the surgical instrument data controller 100. Accordingly, the surgical instrument data controller 100 can be configured in a variety of ways.

Figure 4:
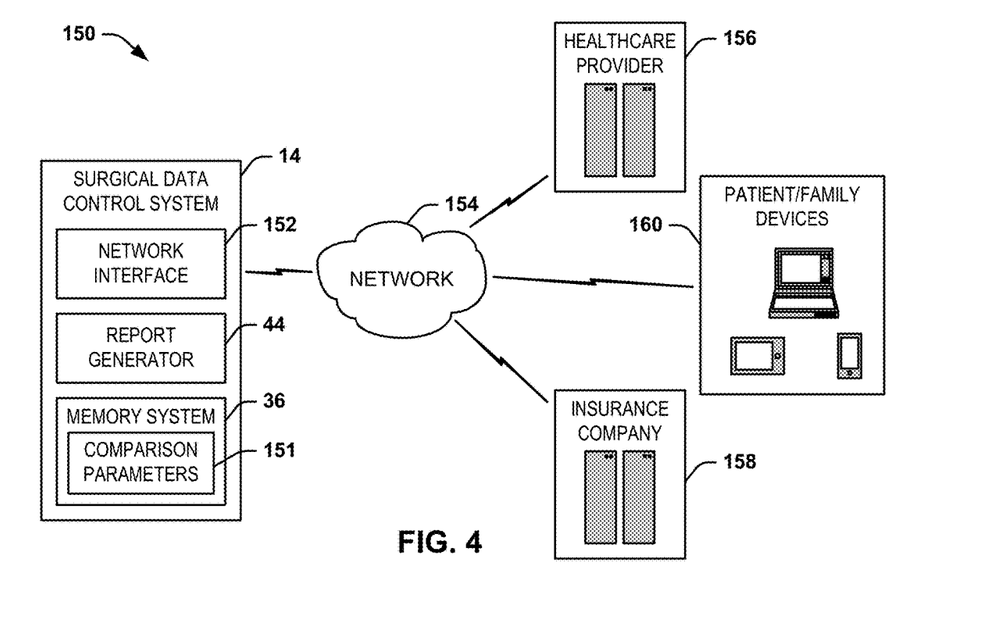
FIG. 4 illustrates an example diagram of dissemination of a surgical dashboard report.

FIG. 4 illustrates an example diagram 150 of dissemination of the surgical dashboard report 46. The diagram 150 demonstrates a portion of the surgical data control system 14 that is implemented in the surgical system in the example of FIG. 1. Therefore, reference is to be made to the example of FIG. 1 in the following description of the example of FIG. 4.

In the example of FIG. 4, the surgical data control system 14 includes the report generator 44 that is configured to access the data stored in the memory system 36, such as immediately upon conclusion of the surgical procedure to aggregate the set of data stored in the memory system 36. As described previously, the aggregation of the set of data stored in the memory system 36 can provide a relationship between substantially all aspects of the surgical procedure, with respect to the patient data, the surgeon data, the staff data, and all of the surgical device data (e.g., including the surgical instrument data transmitted from the transceiver 108 of the surgical instrument data controllers 100 of the surgical instruments 28). As described previously, the aggregation performed by the report generator 44 can associate temporal data and unique identifiers associated with the video monitoring equipment 20, the medicine administering equipment 22, the robotic equipment 24, the anesthesia equipment 26, the surgical instruments 28, the operation environment equipment 30, and the energy providing devices 32 to the surgeon(s) and/or staff and to the patient to provide interrelationships therein.

In addition, in the example of FIG. 4, the memory system 36 is configured to store comparison parameters 151 that can correspond to at least one of a predetermined threshold associated with the surgical device data, such as described previously with respect to the real-time data monitor 38 and surgical feedback system 40, as well as surgical device data and/or other data regarding a previous surgery (e.g., as associated with a different or the same patient/surgeon(s)/staff). Accordingly, the report generator 44 can be further configured to provide comparison data associated with the surgical device data of the immediate surgery of the patient 12 relative to the comparison parameters 151.

Upon aggregating the data stored in the memory system 36, the report generator 44 can generate a surgical dashboard report 46 of the surgical procedure. The surgical dashboard report 46 can provide the aggregated data set in a single data source, such as a URL or a data file (e.g., PDF) that is widely accessible via substantially any computer system. In the example of FIG. 4, the surgical data control system 14 also includes a network interface 152 that is configured to provide coupling of the surgical data control system 14 to a network 154, which can be a local area network (LAN) or a wide area network (WAN), such as the Internet. Therefore, in the example of FIG. 4, the surgical data control system 14 can transmit the surgical dashboard report 46 via the network 154 to one or more enterprise servers associated with a healthcare facility 156, to one or more enterprise servers associated with an insurance company 158 associated with the patient 12, and/or to one or more computer devices 160 associated with the patient/family (e.g., personal computer, laptop computer, tablet computer, smart-phone, etc.), such as belonging to the patient 12 and/or to one or more patient-authorized other people. Accordingly, the surgical dashboard report 46 that provides a complete report of the relationship between substantially all aspects of the surgical procedure, with respect to the patient data, the surgeon data, the staff data, and all of the surgical device data, can be generated and transmitted to all necessary parties substantially immediately (e.g., within one or a few seconds) after conclusion of the surgical procedure.

Figure 5:
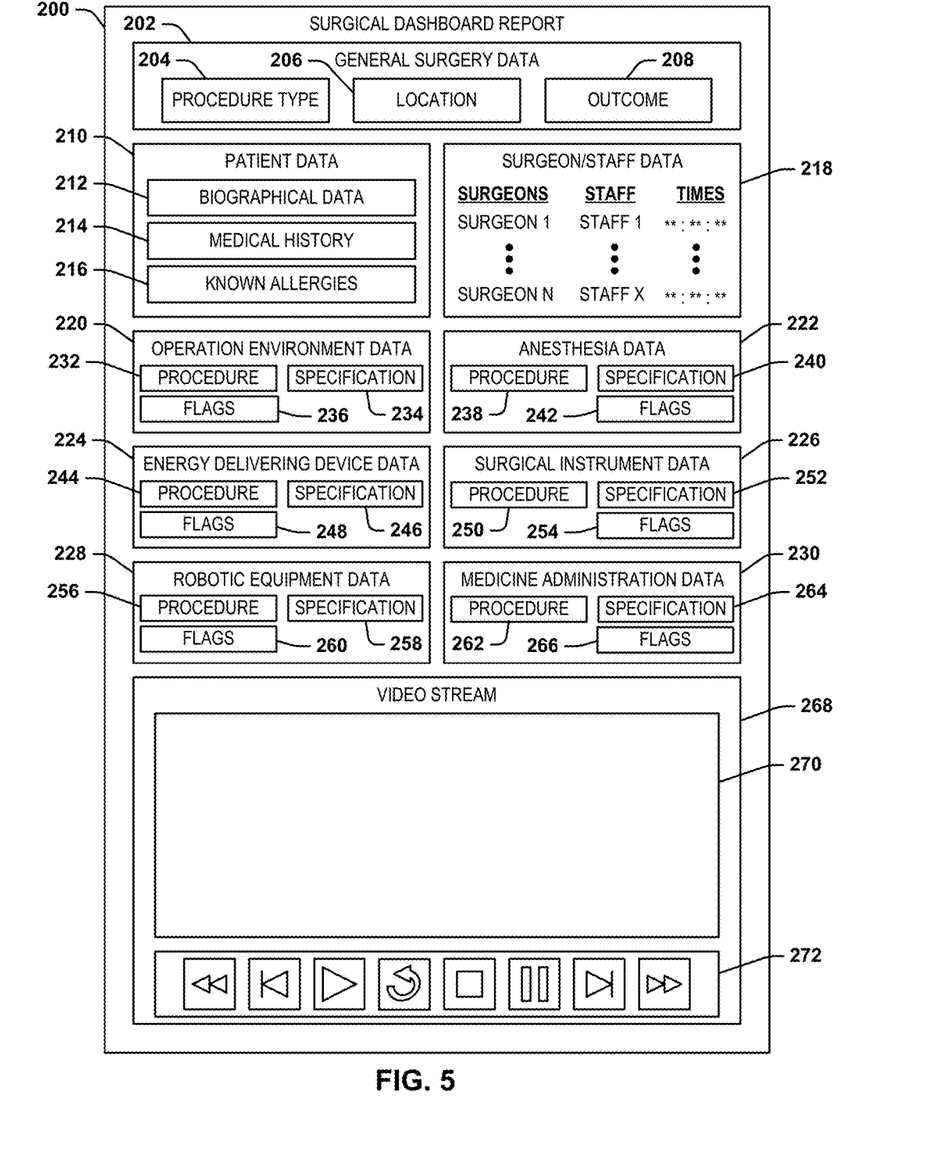
FIG. 5 illustrates an example diagram of a surgical dashboard report.

FIG. 5 illustrates an example of a surgical dashboard report 200. The surgical dashboard report 200 can correspond to the surgical dashboard report 46 in the example of FIG. 1. The surgical dashboard report 200 can include substantially all data that is pertinent to the surgical procedure performed on the patient 12. Therefore, reference is to be made to the examples of FIGS. 1-4 in the following description of the example of FIG. 5.

The surgical dashboard report 200 includes general surgery data 202 that can provide a cursory and general description of the surgical procedure. In the example of FIG. 5, the general surgery data 202 includes a procedure type field 204 that defines the surgical procedure that was performed on the patient 12. The general surgery data 202 also includes a location field 206 that defines the healthcare facility in which the surgical procedure was performed. The general surgery data 202 further includes outcome data 208 that defines the result of the surgical procedure (e.g., success, failure, complications, etc.).

The surgical dashboard report 200 also includes patient data 210 that includes a variety of information regarding the patient 12. In the example of FIG. 5, the patient data 210 includes biographical data 212 associated with the patient 12, which can include metrics that include age, height, weight, mass-body index (BMI), insurance information, family contacts, etc. associated with the patient 12. The patient data 210 also includes medical history data 214 (e.g., prior procedures, past and current medication, family history, etc.), and/or known allergies 216. As an example, the real-time data monitor 38 can be configured to indicate a conflict with respect to the allergies to which the patient 12 may have to substantially mitigate allergic reactions (e.g., to medication, latex, etc.).

The surgical dashboard report 200 also includes surgeon/staff data 218. The surgeon/staff data 218 can include data regarding one or more surgeons (demonstrated as a plurality N of surgeons, where N is a positive integer) that are performing the surgical procedure. The surgeon/staff data 218 can also include data associated with surgical staff, demonstrated as a plurality X of staff members, where X is a positive integer, such as nurses, assistants, operating room maintenance, and the like, that are assisting with the surgical procedure. In addition, the surgeon/staff data 218 includes time-stamps that demonstrate times that the respective surgeon/staff was active during the surgical procedure. As another example, the surgical dashboard report 200 can include hyperlinks to provide access to additional information associated with the surgeons/staff, such as biographical and experience information that can be accessed via the network (e.g., the network 154).

In the example of FIG. 5, the surgical dashboard report 200 includes operation environment data 220, anesthesia data 222, energy delivering device data 224, surgical instrument data 226, robotic equipment data 228, and medicine administration data 230. The operation environment data 220 can correspond to the equipment associated with maintaining or providing the surgical environment. As an example, the surgical environment can correspond to an operating room, such that the operation environment data 220 can an amount of illumination, temperature, humidity, air purity, or other environmental factors. In the example of FIG. 5, the operation environment data 220 includes procedure data 232 that is collected during the surgical procedure of the patient 12. The procedure data 232 can correspond to timing data that is aligned with the environment data, and can include maintenance data and an indication of the surgeon/staff that was present during the surgical procedure that may have adjusted the operation environment equipment 30. The operation environment data 220 can also include specification data 234, such as corresponding to the comparison parameters 151 in the example of FIG. 4, and flags 236. The flags 236 can correspond to indications of operation of the procedure data 232 outside of the specifications defined by the predetermined threshold of operation or the specification data 234. Accordingly, the operation environment data 220 can provide a relationship between the operation environment equipment 30, time and characteristics of use, and the surgeon/staff during the surgical procedure. In addition, the procedure data 232, the specification data 234, and the flags 236 of the operation environment data 220 can include hyperlinks to expand upon the information provided in the surgical dashboard report 200, such as by directing a computer system to a URL via the network 154.

The anesthesia data 222 can correspond to administration of anesthetic to the patient 12 to numb at least a portion of the anatomy of the patient 12 or to induce a sleeping state of the patient 12. For example, the anesthesia data 222 can include amounts of IV medication administering equipment that can be configured to track a volume of anesthetic that is administered to the patient 12, as well as vital signs of the patient 12, such as heart rate, respiration, blood-pressure, or any of a variety of other vital information with respect to the patient. In the example of FIG. 5, the anesthesia data 222 includes procedure data 238 that is collected during the surgical procedure of the patient 12. The procedure data 238 can correspond to timing data that is aligned with the administration of anesthetic to the patient 12, and can include data and an indication of the surgeon/staff that was present during the surgical procedure that may have adjusted the anesthesia equipment 26. The anesthesia data 222 can also include specification data 240, such as corresponding to the comparison parameters 151 in the example of FIG. 4, and flags 242. The flags 242 can correspond to indications of operation of the procedure data 238 outside of the specifications defined by the predetermined threshold of operation or the specification data 240. Accordingly, the anesthesia data 222 can provide a relationship between the anesthesia equipment 26, time and characteristics of use, and the surgeon/staff during the surgical procedure. In addition, the procedure data 238, the specification data 240, and the flags 242 of the anesthesia data 222 can include hyperlinks to expand upon the information provided in the surgical dashboard report 200, such as by directing a computer system to a URL via the network 154.

The energy delivering device data 224 can correspond to data associated with cautery devices that are implemented to cauterize a wound or incision of the patient 12 during the surgical procedure. As another example, the energy delivering device data 224 can correspond to data associated with radiology equipment that provides imaging of the patient 12 during the surgical procedure. In the example of FIG. 5, the energy delivering device data 224 includes procedure data 244 that is collected during the surgical procedure of the patient 12. The procedure data 244 can correspond to timing data that is aligned with the use of the energy providing devices 32 with respect to the patient 12, and can include data and an indication of the surgeon/staff that was present during the surgical procedure that may have used the energy providing devices 32. The energy delivering device data 224 can also include specification data 246, such as corresponding to the comparison parameters 151 in the example of FIG. 4, and flags 248. The flags 248 can correspond to indications of operation of the procedure data 244 outside of the specifications defined by the predetermined threshold of operation or the specification data 246. Accordingly, the energy delivering device data 224 can provide a relationship between the energy providing devices 32, time and characteristics of use, and the surgeon/staff during the surgical procedure. In addition, the procedure data 244, the specification data 246, and the flags 248 of the energy delivering device data 224 can include hyperlinks to expand upon the information provided in the surgical dashboard report 200, such as by directing a computer system to a URL via the network 154.

The surgical instrument data 226 can correspond to the surgical instrument data that is transmitted from each of the surgical instruments 28, such as via respective surgical instrument data controllers 100 associated with each of the surgical instruments 28. Thus, the surgical instrument data 226 can be transmitted from any of a variety of hand-held and other surgical instruments that are implemented or manipulated by the surgeon(s) or staff during the surgical procedure, and can thus correspond to at least one metric associated with performance and function of the respective surgical instrument 28. As an example, the surgical instrument data 226 can include at least one of pressure, torque, or tension associated with the manipulation of the respective surgical instrument on the patient 12. As another example, the surgical instrument data 226 can correspond to a detected tissue type (e.g., bone, muscle, skin, fat, etc.) of the patient 12 during use of a respective surgical instrument 28. As yet another example, the surgical instrument data 226 can include position of the surgical instrument 28 in three-dimensional space or relative to a reference position, or to detected motion (e.g., hand tremors) of the respective surgical instrument 28.

In the example of FIG. 5, the surgical instrument data 226 includes procedure data 250 that is collected during the surgical procedure of the patient 12. The procedure data 250 can correspond to timing data that is aligned with the use of the surgical instruments 28 with respect to the patient 12, and can include data and an indication of the surgeon/staff that was present during the surgical procedure that may have used the surgical instruments 28. The surgical instrument data 226 can also include specification data 252, such as corresponding to the comparison parameters 151 in the example of FIG. 4, and flags 254. The flags 254 can correspond to indications of operation of the procedure data 250 outside of the specifications defined by the predetermined threshold of operation or the specification data 252. Accordingly, the surgical instrument data 226 can provide a relationship between the surgical instruments 28, time and characteristics of use, and the surgeon/staff during the surgical procedure. In addition, the procedure data 250, the specification data 252, and the flags 254 of the surgical instrument data 226 can include hyperlinks to expand upon the information provided in the surgical dashboard report 200, such as by directing a computer system to a URL via the network 154.

The robotic equipment data 228 can correspond to data associated with one or more electro-mechanical devices or components that are configured to assist the surgeon(s) during the surgical procedure, such as from the robotic equipment 24. As an example, robotic equipment data 228 can be associated with pressure or torque applied to hold open a wound or incision, movement of large medical equipment throughout the surgical environment, adjustments to the position of the patient, or any of a variety of other functions that require mechanical motion or stability via the robotic equipment 24. In the example of FIG. 5, the robotic equipment data 228 includes procedure data 256 that is collected during the surgical procedure of the patient 12. The procedure data 256 can correspond to timing data that is aligned with the use of the robotic equipment 24 with respect to the patient 12, and can include data and an indication of the surgeon/staff that was present during the surgical procedure that may have used, programmed, or adjusted the energy robotic equipment 24. The robotic equipment data 228 can also include specification data 258, such as corresponding to the comparison parameters 151 in the example of FIG. 4, and flags 260. The flags 260 can correspond to indications of operation of the procedure data 256 outside of the specifications defined by the predetermined threshold of operation or the specification data 258. Accordingly, the robotic equipment data 228 can provide a relationship between the robotic equipment 24, time and characteristics of use, and the surgeon/staff during the surgical procedure. In addition, the procedure data 256, the specification data 258, and the flags 260 of the robotic equipment data 228 can include hyperlinks to expand upon the information provided in the surgical dashboard report 200, such as by directing a computer system to a URL via the network 154.

The medicine administration data 230 can correspond to data associated with the administration of medication to the patient 12 during the surgical procedure. For example, the medicine administration data 230 can characterize a volume of liquid or gas that is administered to the patient 12 via the medicine administering equipment 22, such as including IV or gaseous medication or oxygen that is administered to the patient 12. In the example of FIG. 5, the medicine administration data 230 includes procedure data 262 that is collected during the surgical procedure of the patient 12. The procedure data 262 can correspond to timing data that is aligned with the use of the medicine administering equipment 22 with respect to the patient 12, and can include data and an indication of the surgeon/staff that was present during the surgical procedure that may have used or adjusted the medicine administering equipment 22. The medicine administration data 230 can also include specification data 264, such as corresponding to the comparison parameters 151 in the example of FIG. 4, and flags 266. The flags 266 can correspond to indications of operation of the procedure data 262 outside of the specifications defined by the predetermined threshold of operation or the specification data 264. Accordingly, the medicine administration data 230 can provide a relationship between the medicine administering equipment 22, time and characteristics of use, and the surgeon/staff during the surgical procedure. In addition, the procedure data 262, the specification data 264, and the flags 266 of the medicine administration data 230 can include hyperlinks to expand upon the information provided in the surgical dashboard report 200, such as by directing a computer system to a URL via the network 154.

In addition, the surgical dashboard report 200 includes a video stream portion 268. As an example, the video stream portion 268 can enable viewing of a video stream of at least a portion of the surgical procedure via an active video stream monitor 270 in the example of the surgical dashboard report 200 being provided on a GUI via a URL (e.g., as part of a website associated with the respective healthcare provider). As another example, while the example of FIG. 5 demonstrates the video stream monitor 270 as being a part of the surgical dashboard report 200, the video stream portion 268 can alternatively be accessible via a hyperlink associated with the surgical dashboard report 200 being arranged as a PDF document having been transmitted (e.g., emailed) to one or more destination devices. The video stream portion 268 can thus enable a viewer of the surgical dashboard report 200 to consume a video stream corresponding to one or more portions of the surgical procedure of the patient 12, such as based on video data that is wirelessly transmitted to the surgical data control system 14 from the video monitoring equipment 20 during the surgical procedure.

As an example, the video stream portion 268 can be configured to facilitate playback of video streams of one or more recording devices that had monitored the surgical procedure, such as from different angle perspectives. The video stream portion 268 can also facilitate playback of video streams taken from camera devices associated with probes (e.g., catheters or scopes) that had captured a video feed of internal portions of the anatomy of the patient 12. In the example of FIG. 5, the video stream portion 268 includes video controls 272 that can be manipulated by a viewer of the surgical dashboard report 200 to facilitate play, stop, pause, chapter selection, fast-forward, rewind, or any of a variety of other controls to enable the user to view the video stream(s) associated with the surgical procedure from the surgical dashboard report 200. Additionally, the video stream portion 268 can include embedded audio, or can include separate playback of audio, such as may be disconnected with respect to the video streams (e.g., real-time audio recording of the surgical procedure, dictated notes provided by the surgeon(s) or the staff, or of the patient 12. Furthermore, the video stream portion 268 can facilitate the viewing of static, still photographs of the surgical procedure. Accordingly, the video stream portion 268 provides another manner of presenting the surgical procedure to the users of the surgical dashboard report 200, such within one second or a few seconds after conclusion of the surgical procedure.

Figure 6:
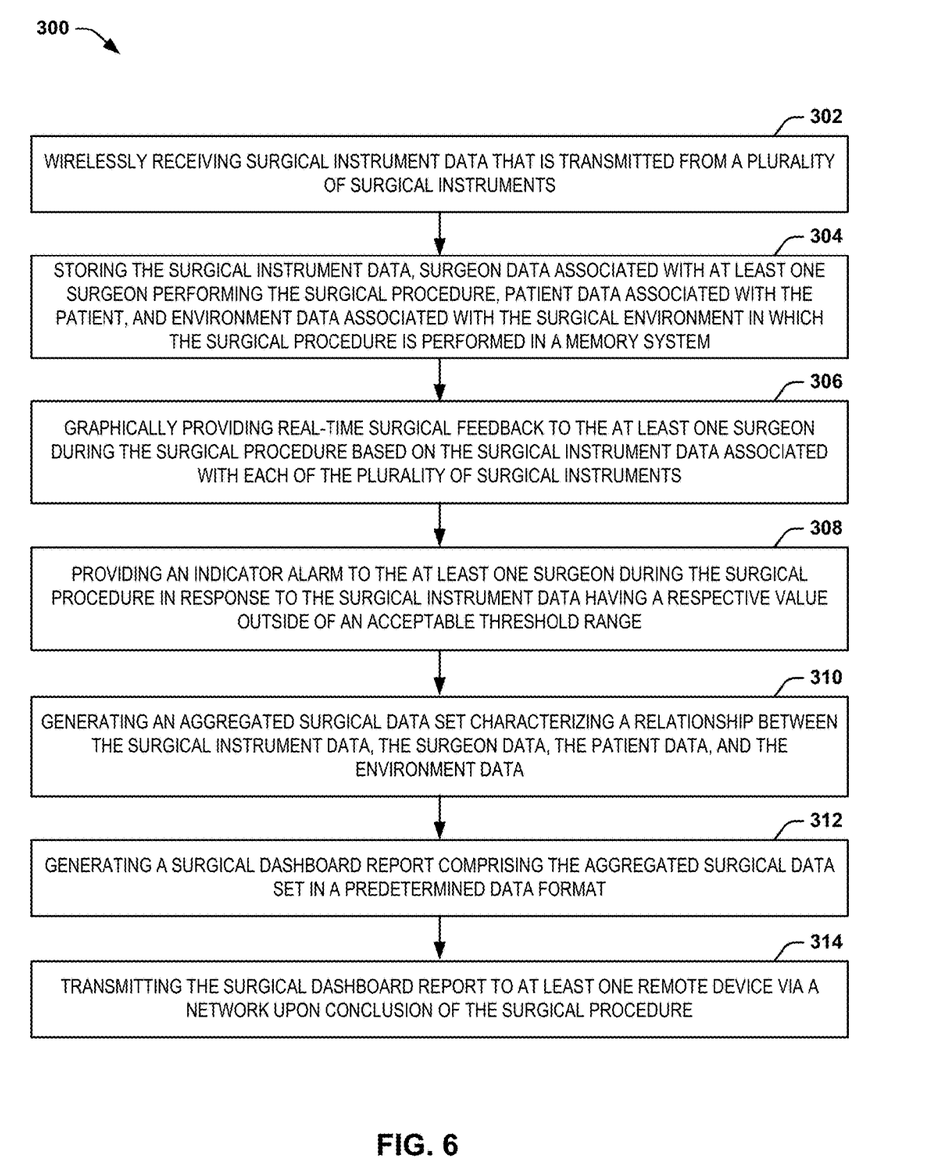
FIG. 6 illustrates an example of a method for providing feedback for a surgical procedure performed by at least one surgeon.

In view of the foregoing structural and functional features described above, a methodology in accordance with various aspects of the example embodiments will be better appreciated with reference to FIG. 6. While, for purposes of simplicity of explanation, the methodologies of FIG. 6 are shown and described as executing serially, it is to be understood and appreciated that the example embodiments are not limited by the illustrated order, as some aspects could, in accordance with the example embodiments, occur in different orders and/or concurrently with other aspects from that shown and described herein. Moreover, not all illustrated features may be required to implement a methodology in accordance with an aspect of the example embodiments.

FIG. 6 illustrates an example of a method 300 for providing feedback for a surgical procedure performed by at least one surgeon. At 302, surgical instrument data (e.g., the procedure data 250 of the surgical instrument data 226) that is transmitted from a plurality of surgical instruments (e.g., the surgical instruments 28) is wirelessly received. The surgical instrument data from each of the plurality of surgical instruments can characterize at least one of pressure, tension, and torque associated with use of the respective one of the plurality of surgical instruments by a given surgeon of the at least one surgeon during the surgical procedure. At 304, the surgical instrument data, surgeon data associated with at least one surgeon performing the surgical procedure (e.g., included in the surgeon/staff data 218), patient data associated with the patient (e.g., included in the patient data 210), and environment data associated with the surgical environment in which the surgical procedure is performed (e.g., included in the procedure data 232 of the operation environment data 220) is stored in a memory system (e.g., the memory system 36). At 306, real-time surgical feedback is graphically provided to the at least one surgeon during the surgical procedure (e.g., via the real-time data monitor 38 and the surgical feedback system 40) based on the surgical instrument data associated with each of the plurality of surgical instruments. At 308, an indicator alarm is provided to the at least one surgeon (e.g., via the alarm(s) 42) during the surgical procedure in response to the surgical instrument data having a respective value outside of an acceptable threshold range (e.g., based on the comparison parameters 151). At 310, an aggregated surgical data set characterizing a relationship between the surgical instrument data, the surgeon data, the patient data, and the environment data is generated. At 312, a surgical dashboard report (e.g., the surgical dashboard report 46 and/or the surgical dashboard report 200) comprising the aggregated surgical data set is generated in a predetermined data format (e.g., in a PDF format). At 314, the surgical dashboard report is transmitted to at least one remote device (e.g., to a healthcare facility 156, an insurance company 158, and/or to computer device(s) 160 associated with the patient/family) via a network upon conclusion of the surgical procedure.

What have been described above are examples of the example embodiments. It is, of course, not possible to describe every conceivable combination of components or methodologies for purposes of describing the example embodiments, but one of ordinary skill in the art will recognize that many further combinations and permutations of the example embodiments are possible. Accordingly, the example embodiments are intended to embrace all such alterations, modifications and variations that fall within the spirit and scope of the appended claims.

What is claimed is:

1. A surgical data control system comprising:
a wireless data receiver configured to receive surgical device data, the surgical device data comprising:
surgical instrument data transmitted from a plurality of surgical instruments, the surgical instrument data from each of the plurality of surgical instruments characterizing at least one metric corresponding to performance and function of a respective one of the plurality of surgical instruments during a surgical procedure on a patient;
medicine administration data transmitted from medicine administering equipment, the medicine administration data characterizing at least one of dosage and time of medicine administered to the patient via the medicine administering equipment during the surgical procedure; and
energy data transmitted from at least one energy providing device, the energy data characterizing operation of the at least one energy providing device during the surgical procedure;
a memory system configured to store the surgical device data, surgeon data of at least one surgeon performing the surgical procedure, patient data corresponding to the patient, and environment data of an operating room in which the surgical procedure is performed, the environment data comprising at least one of temperature data, light intensity data, and humidity data of the operating room; and
a report generator configured to generate an aggregated surgical data set characterizing a relationship between the surgical device data, the surgeon data, the patient data, and the environment data, and to generate a surgical dashboard report comprising the aggregated surgical data set in a predetermined data format, the surgical data control system being configured to transmit the surgical dashboard report to at least one remote device via a network upon conclusion of the surgical procedure.

2. The system of claim 1, wherein the report generator is configured to aggregate the surgical data set with temporal data and unique identifiers of each of the plurality of surgical instruments, the medicine administering equipment, and the at least one energy providing device to the at least one surgeon to provide a relationship between the surgical instrument data, the medicine administration data, and the energy data, relative to the at least one surgeon based on the temporal data and the unique identifiers.

3. The system of claim 1, further comprising a real-time data monitor that is configured to monitor the surgical device data during the surgical procedure, to provide real-time surgical feedback to the at least one surgeon during the surgical procedure, and to provide an indicator alarm to the at least one surgeon during the surgical procedure in response to at least one of the surgical instrument data, the medicine administration data, and the energy data having a respective value outside of an acceptable threshold range.

4. The system of claim 1, wherein the surgical instrument data includes at least one of pressure, tension, and torque of each of the plurality of surgical instruments during the surgical procedure.

5. The system of claim 1, wherein each of the plurality of surgical instruments comprises a surgical instrument data controller, the surgical instrument controller comprising:
a registration component configured to register a given surgeon or staff to the respective one of the plurality of surgical instruments during use of the respective one of the plurality of surgical instruments in the surgical procedure;
a data collection sensor configured to measure the surgical instrument data of the respective one of the plurality of surgical instruments;
a real-time clock configured to provide time-stamp data corresponding to at least one of the registration of the given surgeon to the respective one of the plurality of surgical instruments and the surgical instrument data of the respective one of the plurality of surgical instruments; and
a transceiver configured to transmit the surgical instrument data of the respective one of the plurality of surgical instruments to the surgical data control system.

6. The system of claim 5, wherein the surgical instrument data controller is adapted to be mechanically coupled to the respective one of the plurality of surgical instruments.

7. The system of claim 5, wherein the transceiver is further configured to receive threshold data corresponding to a predetermined threshold range of operation with respect to the surgical instrument data of the respective one of the plurality of surgical instruments transmitted from the surgical data control system, wherein the surgical instrument controller further comprises a local feedback component configured to monitor the surgical instrument data of the respective one of the plurality of surgical instruments during the surgical procedure, to provide real-time feedback of the surgical instrument data of the respective one of the plurality of surgical instruments to the given surgeon during the surgical procedure, and to provide an indicator alarm to the given surgeon during the surgical procedure in response to the surgical instrument data being outside of the predetermined threshold range of operation.

8. The system of claim 1, wherein the surgical device data further comprises video data transmitted from video monitoring equipment, the video data corresponding to a video stream of at least a portion of the surgical procedure, wherein the surgical dashboard report further comprises at least one of a graphical user interface (GUI) component configured to facilitate playback of the video stream and a uniform resource locator (URL) configured to access the video stream via the network.

9. The system of claim 1, wherein the surgical device data further comprises anesthesia data transmitted from anesthesia equipment, the anesthesia data characterizing at least one an amount of anesthetic that is administered to the patient, a type of anesthetic that is administered to the patient, and vital information of the patient.

10. The system of claim 1, wherein the memory system is further configured to store staff data of at least one surgical staff member assisting with the surgical procedure, and wherein the report generator is configured to generate the aggregated surgical data set characterizing a relationship between the surgical device data, the surgeon data, the staff data, the patient data, and the environment data.

11. The system of claim 1, wherein the surgical data control system is configured to generate the surgical dashboard report in a portable document format (PDF) format in response to conclusion of the surgical procedure, and wherein the surgical data control system is configured to transmit the surgical dashboard report to at least one of a data server of an associated healthcare provider, a data server of an associated insurance company, and a computer corresponding to at least one of the patient and patient-authorized people.

12. The system of claim 11, wherein the surgical dashboard report comprises hyperlinks linking to the aggregated surgical data set that facilitate access to expanded data corresponding to the aggregated surgical data set via a network.

13. The system of claim 1, wherein the surgical dashboard report further comprises a plurality of indicator flags corresponding to the surgical instrument data, the medicine administration data, and the energy data, the plurality of indicator flags providing an indication as to at least one of the surgical instrument data, the medicine administration data, and the energy data having a respective value outside of an acceptable threshold range at a defined duration of time during the surgical procedure.

14. A surgical system comprising a plurality of surgical instruments, each of the plurality of surgical instruments comprising a surgical instrument data controller, the surgical instrument controller comprising:
a registration component configured to register a given surgeon or staff to the respective one of the plurality of surgical instruments during use of the respective one of the plurality of surgical instruments by the given surgeon in a surgical procedure;
a data collection sensor configured to measure surgical instrument data comprising at least one of pressure, tension, and torque corresponding to use of the respective one of the plurality of surgical instruments by the given surgeon during the surgical procedure;
a real-time clock configured to provide time-stamp data corresponding to at least one of the registration of the given surgeon to the respective one of the plurality of surgical instruments and the surgical instrument data of the respective one of the plurality of surgical instruments; and
a transceiver configured to transmit the surgical instrument data of the respective one of the plurality of surgical instruments to a surgical data control system, the surgical data control system being configured to store the surgical instrument data and to store environment data comprising at least one of temperature data, light intensity data, and humidity data of the operating room for reporting and feedback of the surgical procedure.

15. The system of claim 14, wherein the surgical instrument data controller is adapted to be mechanically coupled to the respective one of the plurality of surgical instruments.

16. The system of claim 14, wherein the transceiver is further configured to receive threshold data for a predetermined threshold range of operation with respect to the surgical instrument data of the respective one of the plurality of surgical instruments transmitted from the surgical data control system, wherein the surgical instrument controller further comprises a local feedback component configured to monitor the surgical instrument data of the respective one of the plurality of surgical instruments during the surgical procedure, to provide real-time feedback of the surgical instrument data of the respective one of the plurality of surgical instruments to the given surgeon during the surgical procedure, and to provide an indicator alarm to the given surgeon during the surgical procedure in response to the surgical instrument data being outside of the predetermined threshold range of operation.

17. The system of claim 14, wherein the transceiver is further configured to transmit the surgical instrument data of the respective one of the plurality of surgical instruments to a transceiver of another one of the plurality of surgical instruments.

18. A method for providing feedback for a surgical procedure performed by at least one surgeon, the method comprising:
wirelessly receiving surgical instrument data that is transmitted from a plurality of surgical instruments, the surgical instrument data from each of the plurality of surgical instruments characterizing at least one of pressure, tension, and torque corresponding to use of the respective one of the plurality of surgical instruments by a given surgeon of the at least one surgeon during the surgical procedure;
generating surgeon data, the surgeon data comprising a registration of the given surgeon of the at least one surgeon performing the surgical procedure to the respective one of the plurality of surgical instruments during use of the respective one of the plurality of surgical instruments in the surgical procedure;
storing the surgical instrument data, surgeon data of at least one surgeon performing the surgical procedure, patient data of the patient, and environment data of an operating room in which the surgical procedure is performed in a memory system, the environment data comprising at least one of temperature data, light intensity data, and humidity data of the operating room;
graphically providing real-time surgical feedback to the at least one surgeon during the surgical procedure based on the surgical instrument data of each of the plurality of surgical instruments;
providing an indicator alarm to the at least one surgeon during the surgical procedure in response to the surgical instrument data having a respective value outside of an acceptable threshold range;
generating an aggregated surgical data set characterizing a relationship between the surgical instrument data, the surgeon data, the patient data, and the environment data;
generating a surgical dashboard report comprising the aggregated surgical data set in a predetermined data format; and
transmitting the surgical dashboard report to at least one remote device via a network upon conclusion of the surgical procedure.

19. The method of claim 18, further comprising:
wirelessly receiving medicine administration data transmitted from medicine administering equipment, the medicine administration data characterizing at least one of dosage and time of medicine administered to the patient via the medicine administering equipment during the surgical procedure; and wirelessly receiving energy data transmitted from at least one energy providing device, the energy data characterizing operation of the at least one energy providing device during the surgical procedure;

wherein graphically providing real-time surgical feedback comprises graphically providing the real-time surgical feedback to the at least one surgeon during the surgical procedure based on the surgical instrument data of each of the plurality of surgical instruments, based on the medicine administration data, and based on the energy data;

wherein providing the indicator alarm comprises providing the indicator alarm to the at least one surgeon during the surgical procedure in response to at least one of the surgical instrument data, the medicine administration data, and the energy data having a respective value outside of an acceptable threshold range; and wherein generating the aggregated surgical data set comprises generating the aggregated surgical data set characterizing a relationship between the surgical instrument data, the medicine administration data, the energy data, the surgeon data, the patient data, and the environment data.

* * * * *